US010012612B2

(12) United States Patent
Ohtsuka et al.

(10) Patent No.: US 10,012,612 B2
(45) Date of Patent: Jul. 3, 2018

(54) GAS SENSOR ELEMENT AND GAS SENSOR

(71) Applicant: NGK SPARK PLUG CO., LTD., Nagoya-shi, Aichi (JP)

(72) Inventors: Shigehiro Ohtsuka, Gifu (JP); Tomohiro Nishi, Aichi (JP); Keisuke Nakagawa, Kiyosu (JP); Kazuma Ito, Komaki (JP); Ippei Kato, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 184 days.

(21) Appl. No.: 15/207,690

(22) Filed: Jul. 12, 2016

(65) Prior Publication Data

US 2017/0016849 A1    Jan. 19, 2017

(30) Foreign Application Priority Data

Jul. 13, 2015 (JP) ................... 2015-139520

(51) Int. Cl.
| | | |
|---|---|---|
| *G01N 27/12* | (2006.01) | |
| *G01N 27/30* | (2006.01) | |
| *G01N 27/406* | (2006.01) | |
| *G01N 27/407* | (2006.01) | |
| *G01D 11/30* | (2006.01) | |
| *G01N 27/419* | (2006.01) | |

(52) U.S. Cl.
CPC ......... *G01N 27/4076* (2013.01); *G01D 11/30* (2013.01); *G01N 27/4073* (2013.01); *G01N 27/419* (2013.01)

(58) Field of Classification Search
CPC .... G01N 27/125; G01N 27/30; G01N 27/304; G01N 27/406; G01N 27/407; G01N 27/4071; G01N 27/4073; G01N 27/4074; G01N 27/4075; G01N 27/4076
See application file for complete search history.

(56) References Cited

U.S. PATENT DOCUMENTS

| | | | | |
|---|---|---|---|---|
| 5,527,633 | A | * 6/1996 | Kawasaki | .............. C23C 4/06 429/495 |
| 9,136,033 | B2 | 9/2015 | Kozuka et al. | |
| 2012/0021334 | A1 | * 1/2012 | Kobayashi | .......... H01M 4/8835 429/489 |

FOREIGN PATENT DOCUMENTS

| | | |
|---|---|---|
| JP | 06-329463 A * | 11/1994 |
| JP | 3417090 B2 | 6/2003 |
| JP | 2009-63330 A | 3/2009 |
| WO | WO 2013/150779 A1 | 10/2013 |

* cited by examiner

*Primary Examiner* — Susan D Leong
(74) *Attorney, Agent, or Firm* — Sughrue Mion, PLLC

(57) ABSTRACT

An inside lead portion of a gas sensor element has a lanthanum zirconate layer arranged between an electrically conductive oxide layer and a solid electrolyte member. Meanwhile, an inside detection electrode portion of the gas sensor element is formed such that (i) no lanthanum zirconate layer is formed between an electrically conductive oxide layer and the solid electrolyte member, or (ii) a lanthanum zirconate layer thinner than the lanthanum zirconate layer of the inside lead portion is formed between the electrically conductive oxide layer and the solid electrolyte member.

6 Claims, 10 Drawing Sheets

FIG. 2A
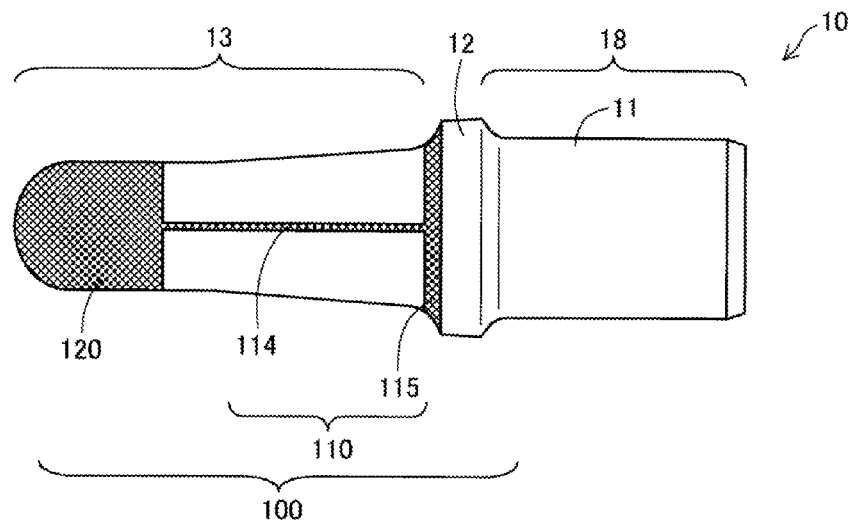
FIG. 2B
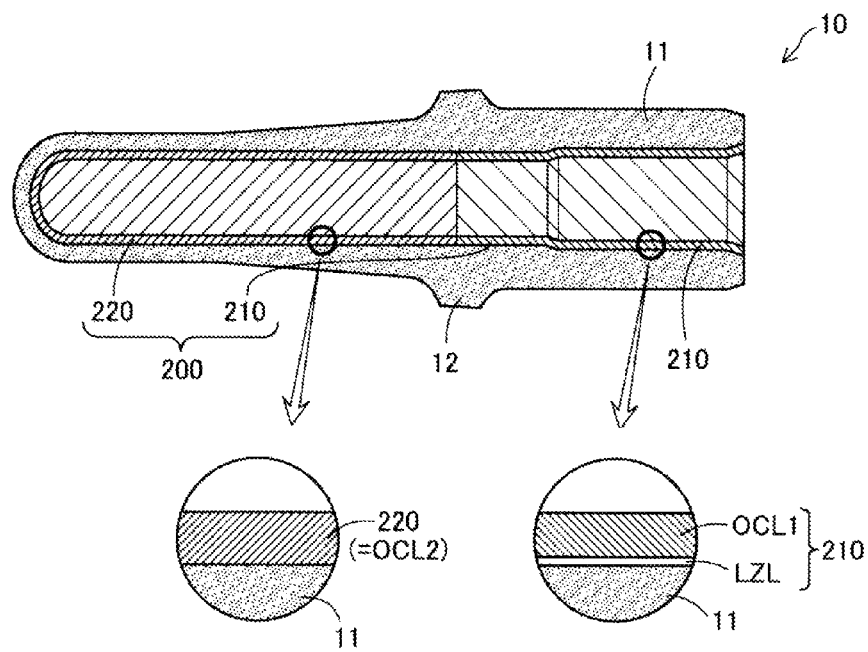
FIG. 2C     FIG. 2D

FIG. 3A
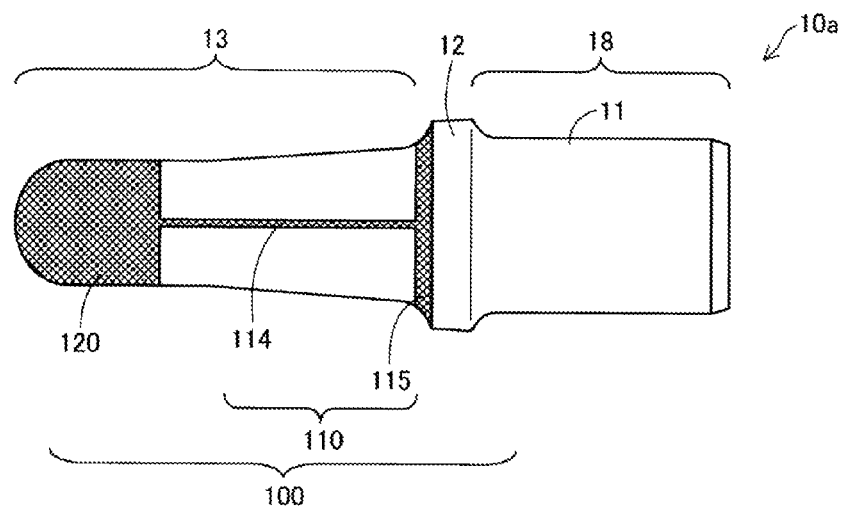
FIG. 3B
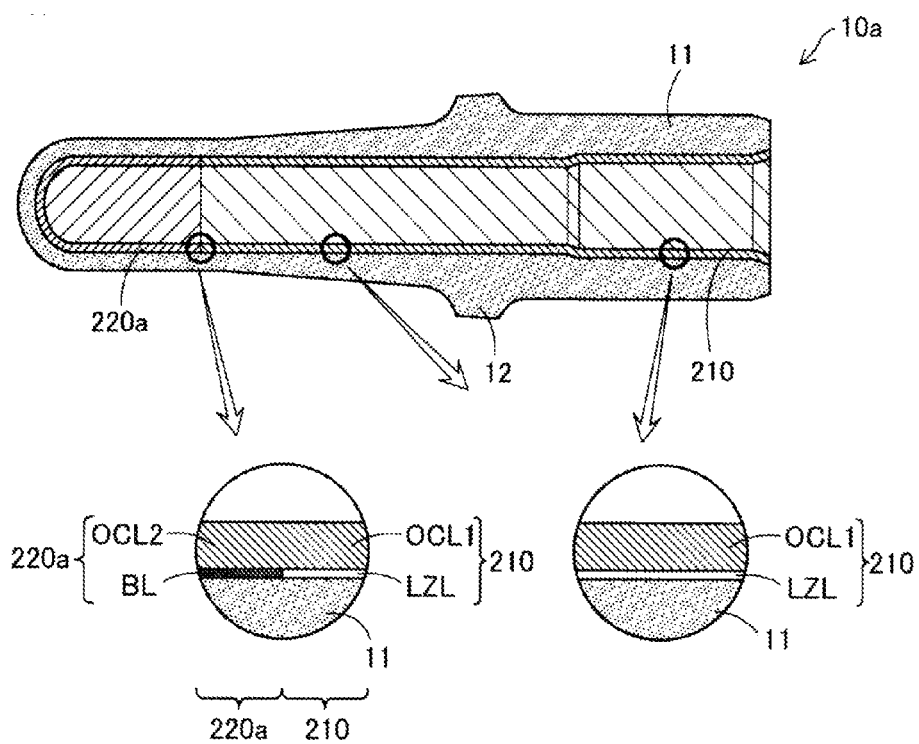
FIG. 3C   FIG. 3D

FIG. 4A
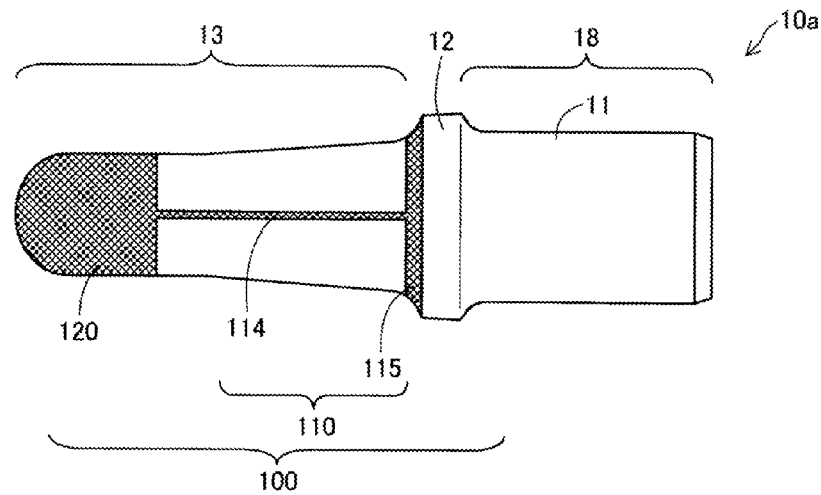
FIG. 4B
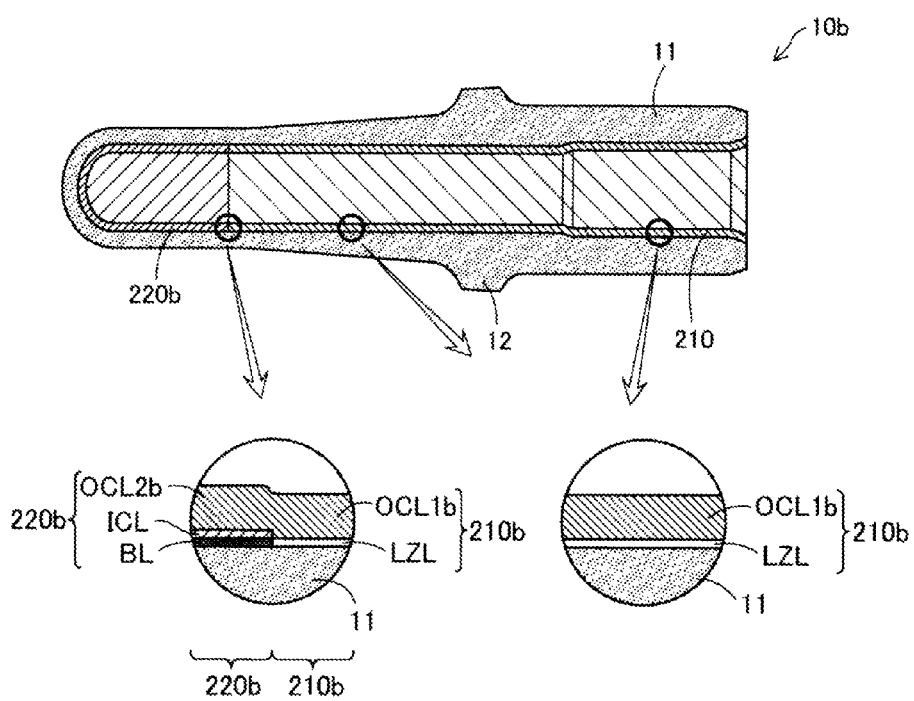
FIG. 4C   FIG. 4D

SAMPLE S01 (Reaction layer LZL provided)

SAMPLE S02 (Reaction layer LZL provided)

SAMPLE S03 (Reaction layer LZL not provided)

SAMPLE S04 (Reaction layer LZL not provided)

GAS SENSOR ELEMENT AND GAS SENSOR

BACKGROUND OF THE INVENTION

1. Field of the Invention

The present invention relates to a gas sensor element which uses electrodes formed of an electrically conductive oxide and to a gas sensor which includes the gas sensor element.

2. Description of the Related Art

Conventionally, a gas sensor has been known which includes a gas sensor element whose electrical characteristic changes with the concentration of a particular gas component contained in a gas under measurement. For example, Patent Document 1 discloses a gas sensor element which includes a solid electrolyte member having the shape of a bottomed tube closed at its forward end; an inside electrode (a reference electrode) formed on the inner surface of the solid electrolyte member; and an outside electrode (a detection electrode) formed on a forward end portion of the outer surface of the solid electrolyte member. Such a gas sensor is suitably used for detecting the concentration of a particular gas contained in exhaust gas discharged from, for example, a combustor or an internal combustion engine. Also, Patent Documents 2 and 3 disclose various types of electrically conductive oxides. These electrically conductive oxides can be used as an electrode material for a gas sensor element.

Incidentally, with the tightening of emission control standards in recent years, the requirements for gas sensors are becoming more severe year by year. The requirements include (i) higher gas detection accuracy, (ii) excellent heat resistance, and (iii) low cost. When the electrically conductive oxides disclosed in Patent Documents 2 and 3 are used as an electrode material for a gas sensor element, electrodes having a sufficiently low electrical resistance are obtained. Thus, it becomes possible to obtain a gas sensor element which has an improved gas detection accuracy, which is inexpensive as compared with the case where only a noble metal is used as an electrode material, and which has excellent heat resistance.

[Patent Document 1] Japanese Patent Application Laid-Open (kokai) No. 2009-63330

[Patent Document 2] Japanese Patent No. 3417090

[Patent Document 3] WO 2013/150779

3. Problems to be Solved by the Invention

As to the electrodes of a gas sensor element, not only low electrical and heat resistance, but also resistance to mechanical impact (impact resistance) is required. Each electrode of a gas sensor element has a detection electrode portion used for gas detection and a lead portion for outputting an output signal from the detection electrode portion to an external circuit. In some cases, the lead portion comes into contact with a connection terminal for electrical connection with the external circuit. In such a case, the lead portion must have a sufficiently high impact resistance. Electrically conductive oxide is brittle and has a low impact resistance as compared with noble metal materials. Therefore, when an electrically conductive oxide is merely used as an electrode material for a gas sensor element, sufficiently high impact resistance cannot be attained. Accordingly, a problem arises in that such a gas sensor element and a gas sensor including the same cannot provide the requisite performance.

SUMMARY OF THE INVENTION

The present invention has been accomplished so as to solve the above-described problems. Further, an object of the present invention is to provide a gas sensor element and gas sensor having sufficient impact resistance even when using an electrically conductive oxide as an electrode or electrode lead.

The above object has been achieved by providing (1) a gas sensor element comprising: a solid electrolyte member extending in an axial direction and containing $ZrO_2$ having oxygen-ion conductivity; an outside electrode provided on one of surfaces of the solid electrolyte member and which comes into contact with a gas under measurement; and an inside electrode provided on an opposing surface of the solid electrolyte member and which comes into contact with a reference gas. The inside electrode includes an inside detection electrode portion disposed on a forward end side in the axial direction and which detects a particular gas contained in the gas under measurement, and an inside lead portion which is disposed rearward of the inside detection electrode portion, which is connected to the inside detection electrode portion, and which comes into contact with a connection terminal for external output. The inside electrode includes an electrically conductive oxide layer whose main component is a perovskite phase which is represented by a composition formula of $La_aM_bNi_cO_x$ (where M is at least one element selected from Co and Fe, a+b+c=1, $1.25 \leq x \leq 1.75$) and has a perovskite-type crystal structure, and the coefficients a, b, and c satisfy $0.459 \leq a \leq 0.535$, $0.200 \leq b \leq 0.475$, and $0.025 \leq c \leq 0.350$. The inside lead portion includes a lanthanum zirconate layer between the electrically conductive oxide layer and the solid electrolyte member, and the inside detection electrode portion is formed such that (i) no lanthanum zirconate layer is formed between the electrically conductive oxide layer and the solid electrolyte member, or (ii) a lanthanum zirconate layer formed between the electrically conductive oxide layer and the solid electrolyte member is thinner than the lanthanum zirconate layer of the inside lead portion.

Since the gas sensor element (1) has a lanthanum zirconate layer between the electrically conductive oxide layer of the inside lead portion and the solid electrolyte member, the adhesion between the electrically conductive oxide layer and the solid electrolyte member which sandwich the lanthanum zirconate layer from both sides is enhanced, whereby the impact resistance of the inside lead portion is improved. Meanwhile, in the inside detection electrode portion, no lanthanum zirconate layer is formed between the electrically conductive oxide layer and the solid electrolyte member, or a lanthanum zirconate layer thinner than the lanthanum zirconate layer of the inside lead portion is formed between the electrically conductive oxide layer and the solid electrolyte member. This configuration where the lanthanum zirconate layer is a high resistance layer can restrain the interface resistance between the inside detection electrode portion and the solid electrolyte member from increasing excessively.

In a preferred embodiment (2) of the gas sensor element (1) above, a reaction prevention layer containing a rare earth element-added ceria as a main component is provided between the inside detection electrode portion and the solid electrolyte member.

According to the above configuration (2), the reaction prevention layer retards the occurrence of a reaction between La in the electrically conductive oxide layer and $ZrO_2$ in the solid electrolyte member. Therefore, even in the case of a gas sensor element in which a lanthanum zirconate layer is formed if the reaction prevention layer is absent, by providing the reaction prevention layer, formation of the lanthanum zirconate layer can be prevented or the thickness of the lanthanum zirconate layer can be reduced. Notably, the expression "containing a rare earth element-added ceria as a main component" means that among its constituent components, a rare earth element-added ceria is contained in the reaction prevention layer in the greatest amount.

In another preferred embodiment (3) of the gas sensor element (2) above, the reaction prevention layer is provided only on the forward end side of the gas sensor element with respect to a holding member which holds the gas sensor element when the gas sensor element is incorporated into a gas sensor.

When the gas sensor element is incorporated into a gas sensor, the gas sensor element may be inserted into a housing such as a metallic shell and held by a holding member such as talc disposed between the housing and the gas sensor element. In such a case, in the gas sensor element, the holding member applies a considerably large compressive stress to the outer surface of a portion of the solid electrolyte member where the holding member is disposed. Meanwhile, due to the influence of this compressive stress, tensile stress acts on the inner surface of the portion of the solid electrolyte member where the holding member is disposed. As a result, the reaction prevention layer may crack. Accordingly, the reaction prevention layer is provided only in a region on the forward end side of the gas sensor element with respect to the holding member. In this case, the tensile stress does not impact the reaction prevention layer, and cracking of the reaction prevention layer can be suppressed.

In yet another preferred embodiment (4), the gas sensor element of any of (1) to (3) above is configured such that the inside detection electrode portion has an intermediate electrically conductive layer formed between the reaction prevention layer and the electrically conductive oxide layer, the electrically conductive oxide layer contains no rare earth element-added ceria and comprises a perovskite phase represented by the composition formula $La_aM_bNi_cO_x$, and the intermediate electrically conductive layer comprises a perovskite phase represented by the composition formula $La_aM_bNi_cO_x$ and a rare earth element-added ceria.

According to configuration (4) above, the electrically conductive oxide layer contains no rare earth element-added ceria. Therefore, the electron conductivity of the electrically conductive oxide layer at room temperature is enhanced, whereby the electrical resistance can be lowered. Meanwhile, since the electrically conductive oxide layer contains no rare earth element-added ceria, the adhesion between the electrically conductive oxide layer and the reaction prevention layer may decrease. However, since the intermediate electrically conductive layer containing the perovskite phase and a rare earth element-added ceria is formed between the reaction prevention layer and the electrically conductive oxide layer, the adhesion between the reaction prevention layer and the electrically conductive oxide layer can be enhanced. In addition, since the intermediate electrically conductive layer of the inside detection electrode portion contains the perovskite phase and a rare earth element-added ceria, it is possible to suppress an excessive increase in interface resistance between the inside detection electrode portion and the solid electrolyte member during measurement of gas concentration.

In yet another preferred embodiment (5), the gas sensor element of any of (1) to (3) above is configured such that the electrically conductive oxide layer contains a first electrically conductive oxide layer which constitutes the inside lead portion and a second electrically conductive oxide layer which constitutes the inside detection electrode portion, each of the first electrically conductive oxide layer and the second electrically conductive oxide layer contains the perovskite phase and a rare earth element-added ceria, and the proportion of the rare earth element-added ceria in the second electrically conductive oxide layer is equal to or greater than the proportion of the rare earth element-added ceria in the first electrically conductive oxide layer.

According to configuration (5) above, the proportion of the rare earth element-added ceria in the electrically conductive oxide layer which constitutes the inside detection electrode portion is increased. Therefore, the inside detection electrode portion has a porous structure, whereby the area of the tri-phase interface increases, and thus the interface resistance can be reduced. Also, in the inside lead portion, since the proportion of the rare earth element-added ceria is decreased, the inside lead portion has a dense structure. As a result, the electron conductivity is improved, and the strength of the inside lead portion is increased, whereby the impact resistance of the inside lead portion is further enhanced.

The present invention can be realized in various forms. For example, the present invention can be realized as a gas sensor element, a gas sensor including the gas sensor element, a gas sensor including the gas sensor element and a holding member for holding the gas sensor element, a method of manufacturing the gas sensor element, or a method of manufacturing the gas sensor.

BRIEF DESCRIPTION OF THE DRAWINGS

FIGS. 2A to 2D are explanatory views showing the structure of a gas sensor element according to one embodiment.

FIGS. 3A to 3D are explanatory views showing the structure of a gas sensor element according to another embodiment.

FIGS. 4A to 4D are explanatory views showing the structure of a gas sensor element according to yet another embodiment.

DESCRIPTION OF REFERENCE NUMERALS AND SYMBOLS

Figure 1:
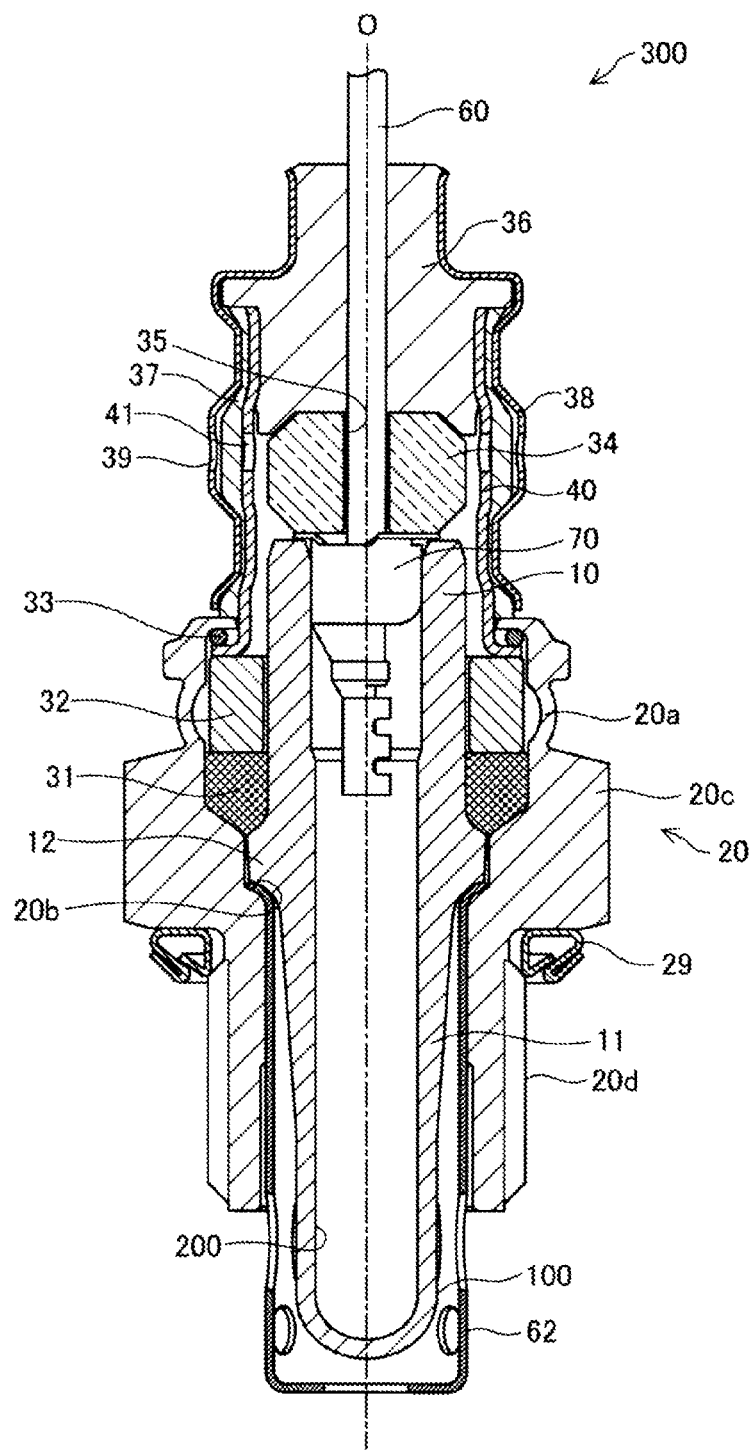
FIG. 1 is a sectional view showing the structure of a gas sensor.

Reference numerals used to identify various features in the drawings include the following.

10, 10*a*, 10*b*: gas sensor element
11: solid electrolyte member
12: flange portion
13: bottomed portion
18: base portion
20: metallic shell
20*a*: bent portion
20*b*: step portion
20*c*: flange portion
20*d*: male screw portion 29: gasket
31: powder charged portion (holding member)
32: insulating member
33: metal ring
34: separator
35: passage hole
36: grommet
37: filter
38: protecting outer tube
39: second vent hole
40: outer tube
41: first vent hole
60: lead wire
62: protector
70: connection terminal
100: outside electrode
110: outside lead portion
114: longitudinal lead portion
115: ring lead portion
120: outside detection electrode portion
200: inside electrode
210: inside lead portion
220, 220a, 220b: inside detection electrode portion
300: gas sensor
BL: reaction prevention layer
ICL: intermediate electrically conductive layer
LZL: lanthanum zirconate layer (reaction layer)
OCL1, OCL1b, OCL2, OCL2b: electrically conductive oxide layer

DETAILED DESCRIPTION OF THE PREFERRED EMBODIMENTS

The invention will next be described in greater detail by reference to the drawings. However, the present invention should be not be construed as being limited thereto.

A. Structure of gas sensor

FIG. 1 is a sectional view showing the structure of a gas sensor 300 according to a first mode of the present invention. The gas sensor 300 has an elongated shape extending along an axial line O. In the flowing description, the lower side of FIG. 1 will be referred to as a forward end side, and the upper side thereof will be referred to as a rear end side. Also, a direction which is orthogonal to the axial line O and is directed outward from the axial line O will be referred to as the "radial direction." The gas sensor 300 is an oxygen concentration sensor and can be used for detecting, for example, the concentration of oxygen contained in exhaust gas discharged from an automobile. The gas sensor 300 includes a gas sensor element 10, a metallic shell 20, a protector 62, an outer tube 40, a protecting outer tube 38, and an electrode wiring structure (electrodes and a lead wire) which will be described below.

The gas sensor element 10 is an oxygen sensor element having a pair of electrodes provided on opposite surfaces of a solid electrolyte member 11 having ion conductivity (oxygen-ion conductivity). The gas sensor element 10 functions as an oxygen concentration cell, and outputs a detection value corresponding to the partial pressure of oxygen. This gas sensor element 10 includes the solid electrolyte member 11 having the shape of a bottomed tube tapered such that its outer diameter decreases toward the forward end; an outside electrode 100 formed on the outer surface of a forward end portion of the solid electrolyte member 11; and an inside electrode 200 (reference electrode) formed on the inner surface of the solid electrolyte member 11. When the gas sensor element 10 is used, a reference gas atmosphere is created in the internal space of the gas sensor element 10, and a gas to be detected is brought into contact with the outer surface of the gas sensor element 10. Gas detection is performed in this state. A lead wire 60 for leading out the detection signal from the inside electrode 200 is extended outward from the rear end of the gas sensor 300. A flange portion 12 protruding in the radial direction is formed at an approximately central portion of the gas sensor element 10 in the axial direction such that the flange portion 12 extends over the entire circumference of the gas sensor element 10.

The metallic shell 20 is a member formed of a metal (e.g., stainless steel) and which surrounds the gas sensor element 10, and a forward end portion of the gas sensor element 10 projects from a forward end portion of the metallic shell 20. The metallic shell 20 has a step portion 20b provided on the inner surface thereof such that the inner diameter decreases toward the forward end. The metallic shell 20 has a polygonal flange portion 20c which is provided at a position near the center of the metallic shell 20 and projects radially outward. An attachment tool such as a hexagonal wrench is engaged with the polygonal flange portion 20c. Further, a male screw portion 20d is formed on the outer surface located on the forward end side of the flange portion 20c. The male screw portion 20d of the metallic shell 20 is attached to a screw hole of an exhaust pipe of, for example, an internal combustion engine, whereby the forward end of the gas sensor element 10 is disposed within the exhaust pipe. Thus, it is becomes possible to detect the concentration of oxygen contained in the gas to be detected (exhaust gas). Further, a gasket 29 is fitted into a recess between a forward-end-side surface of the flange portion 20c and the rear end of the male screw portion 20d. The gasket 29 prevents gas leakage when the gas sensor 300 is attached to the exhaust pipe.

The protector 62 is a tubular member formed of a metal (e.g., stainless steel) and covers the forward end portion of the gas sensor element 10 which projects from the forward end portion of the metallic shell 20. A rear end portion of the protector 62 is bent outward in the radial direction. This rear end portion is held between the forward-end-side surface of the flange portion 12 of the gas sensor element 10 and the step portion 20b of the metallic shell 20, whereby the protector 62 is fixed. When the metallic shell 20 and the gas sensor element 10 are combined together, the protector 62 is inserted into the metallic shell 20 from the rear end side of the metallic shell 20, and the rear end portion of the protector 62 is brought into contact with the step portion 20b of the metallic shell 20. Subsequently, the gas sensor element 10 is inserted into the metallic shell 20 from the rear end side thereof, and the forward-end-side surface of the flange portion 12 is brought into contact with the rear end portion of the protector 62. As described below, a ring lead portion 115 of the outside electrode 100 is provided on the forward-end-side surface of the flange portion 12 of the gas sensor element 10, and the outside electrode 100 electrically communicates with the metallic shell 20 through the ring lead portion 115 and the protector 62. Notably, the protector 62 has a plurality of holes for introducing exhaust gas into the interior of the protector 62. The exhaust gas having flowed into the interior of the protector 62 through the plurality of holes is supplied to the outside electrode 100 as a gas to be detected.

A powder charged portion 31 (corresponding to the holding member in claims) is disposed in a gap between the metallic shell 20 and the rear end of the flange portion 12 of the gas sensor element 10. The powder charged portion 31 is formed by charging a powder material containing talc powder and compressing the charged powder material. The powder charged portion 31 seals the gap between the gas sensor element 10 and the metallic shell 20. A tubular insulating member (ceramic sleeve) 32 is disposed on the rear end side of the powder charged portion 31.

The outer tube 40 is a member formed of a metallic material such as stainless steel, and is joined to the rear end portion of the metallic shell 20 such that the outer tube 40 covers a rear end portion of the gas sensor element 10. A metal ring 33 formed of a metallic material such as stainless steel is disposed between the inner surface of a rear end portion of the metallic shell 20 and the outer surface of a forward end portion of the outer tube 40. The forward end portion of the outer tube 40 is crimped by the rear end portion of the metallic shell 20, whereby the metallic shell 20 and the outer tube 40 are fixed to each other. As a result of the crimping, a bent portion 20a is formed on the rear end side of the flange portion 20c. As a result of forming the bent portion 20a at the rear end portion of the metallic shell 20, the insulating member 32 is pressed toward the forward end side. As a result, the powder charged portion 31 is compressed, whereby the insulating member 32 and the powder charged portion 31 are crimp-fixed, and the gap between the gas sensor element 10 and the metallic shell 20 is sealed.

An insulating separator 34 having an approximately cylindrical shape is disposed inside the outer tube 40. The separator 34 has a passage hole 35 which penetrates the separator 34 in the direction of the axial line O and through which the lead wire 60 is passed. The lead wire 60 is electrically connected to a connection terminal 70. The connection terminal 70 is a member for taking out the sensor output to the outside and is disposed such that it comes into contact with the inside electrode 200. A grommet 36 having an approximately circular columnar shape is disposed inside the outer tube 40 such that the grommet 36 is in contact with the rear end of the separator 34. The grommet 36 has a passage hole which extends along the axial line O and through which the lead wire 60 is passed. The grommet 36 may be formed of, for example, a rubber material such as silicon rubber or fluoro rubber.

The outer tube 40 has a plurality of first vent holes 41 formed in its side wall at a position on the forward end side of the position of the grommet 36 such that the first vent holes 41 are arranged at predetermined intervals in the circumferential direction. A tubular gas-permeable filter 37 is fitted onto the radially outer side of a rear end portion of the outer tube 40 so as to cover the first vent holes 41. Further, the tubular protecting outer tube 38 formed of a metal surrounds the filter 37 from the radially outer side. The protecting outer tube 38 may be formed of, for example, stainless steel. The protecting outer tube 38 has a plurality of second vent holes 39 formed in its side wall such that the second vent holes 39 are arranged at predetermined intervals in the circumferential direction. As a result, an external gas can be introduced into the interior of the outer tube 40 through the second vent holes 39 of the protecting outer tube 38, the filter 37, and the first vent holes 41 of the outer tube 40 and then to the inside electrode 200 of the gas sensor element 10. Notably, the filter 37 is held between the outer tube 40 and the protecting outer tube 38 by crimping the outer tube 40 and the protecting outer tube 38 on the forward end and rear end sides of the second vent holes 39. The filter 37 may be formed of a porous structure of a water-repellent resin such as a fluorocarbon resin. Since the filter 37 is water repellent, the filter 37 allows introduction of a reference gas (the atmosphere) into the space inside the gas sensor element 10 while preventing passage of external water therethrough.

FIG. 2A shows the external appearance of a gas sensor element 10 according to one embodiment. The solid electrolyte member 11 of the gas sensor element 10 has the above-mentioned flange portion 12, a bottomed portion 13 provided on the forward end side (on the left side of FIG. 2A) of the flange portion 12, and a base portion 18 provided on the rear end side of the flange portion 12. The bottomed portion 13 is tapered such that its diameter gradually decreases toward the forward end side, and has a closed forward end. The base portion 18 is a portion which generally has a hollow cylindrical shape and has an opening at its rear end. The outside electrode 100 is formed on the outer surface of the solid electrolyte member 11.

The outside electrode 100 has an outside lead portion 110 and an outside detection electrode portion 120. The outside detection electrode portion 120 is formed to cover the outer surface of a forward-end-side portion of the bottomed portion 13 of the solid electrolyte member 11. The outside detection electrode portion 120 is provided at a position where it comes into contact with a gas under measurement. The outside detection electrode portion 120 constitutes an oxygen concentration cell in cooperation with an inside electrode detection portion (described below) of the inside electrode 200 and the solid electrolyte member 11 and generates an electromotive force (voltage) corresponding to the gas concentration of the gas under measurement.

The outside lead portion 110 is connected to the rear end of the outside detection electrode portion 120. The outside lead portion 110 has a longitudinal lead portion 114 and a ring lead portion 115. The ring lead portion 115 is formed on the forward-end-side surface of the flange portion 12 (at a step portion between the flange portion 12 and the bottomed portion 13) such that the ring lead portion 115 extends over the entire circumference of the gas sensor element 10 and forms an annular shape. The ring lead portion 115 is in electrical contact with the protector 62 (FIG. 1). The longitudinal lead portion 114 is formed to linearly extend along the direction of the axial line O and establish connection between the rear end of the outside detection electrode portion 120 and the ring lead portion 115. Notably, an electrode protection layer (not shown) for protecting the outside detection electrode portion 120 may be formed on the surface of the outside detection electrode portion 120. Notably, the shape and layout of the outside electrode 100 are mere examples, and various other shapes and layouts can be employed.

The solid electrolyte member 11 is formed of a solid electrolyte including $ZrO_2$ which has oxygen-ion conductivity. Generally, a stabilized zirconia including a stabilizer added thereto is used as the solid electrolyte. An oxide selected from yttrium oxide ($Y_2O_3$), calcium oxide (CaO), magnesium oxide (MgO), cerium oxide ($CeO_2$), ytterbium oxide ($Yb_2O_3$), scandium oxide ($Sc_2O_3$), etc., can be used as a stabilizer.

FIG. 2B is a longitudinal sectional view of the gas sensor element 10. As described above, the inside electrode 200 (reference electrode) is provided on the inner surface of the solid electrolyte member 11. The inside electrode 200 has an inside lead portion 210 and an inside detection electrode portion 220.

The inside detection electrode portion 220 is formed to cover the inner surface of a forward-end-side portion of the solid electrolyte member 11. The inside lead portion 210 is connected to the rear end of the inside detection electrode portion 220 and is in contact with the connection terminal 70 (FIG. 1) for electrical connection therewith. The inside detection electrode portion 220 and the inside lead portion 210 as a whole covers substantially the entire inner surface of the solid electrolyte member 11. As described below, the inside lead portion 210 has a higher impact resistance as compared with the inside detection electrode portion 220. In the example of FIG. 2B, the boundary between the inside detection electrode portion 220 and the inside lead portion 210 is located at a position corresponding to the flange portion 12 of the solid electrolyte member 11. As described with reference to FIG. 1, the holding member (the powder charged portion 31) is disposed on the rear end side of the flange portion 12. Preferably, not the inside detection electrode portion 220, but the inside lead portion 210 is formed in an inner surface region located on the rear end side of the flange portion 12 where the powder charged portion 31 is disposed. The reason therefor is as follows. As a result of crimping, a considerably large compressive stress acts on the outer surface of a portion on the rear end side of the flange portion 12 where the powder charged portion 31 is disposed. Thus, a tensile stress acts on the inner surface of the portion on the rear end side of the flange portion 12. As a result, as described below, a reaction prevention layer BL provided on the inside detection electrode portion 220 may crack. In contrast, in the case where the inside lead portion 210 is provided on the inner surface of the portion on the rear end side of the flange portion 12, the reaction prevention layer BL is not subjected to such tensile stress, and cracking of the reaction prevention layer BL can be prevented.

The inside detection electrode portion 220 and the inside lead portion 210 are preferably formed of an electrically conductive oxide layer. Meanwhile, the outside detection electrode portion 120 and the outside lead portion 110 are formed of a noble metal such as platinum (Pt) or a noble metal alloy such as platinum alloy.

FIG. 2C is an explanatory view showing, on an enlarged scale, the sectional structure of the inside detection electrode portion 220. The inside detection electrode portion 220 is constituted by an electrically conductive oxide layer OCL2 formed on the inner surface of the solid electrolyte member 11 and has a single-layer structure. The electrically conductive oxide layer OCL2 preferably contains, as a main component, a crystalline phase (perovskite phase) having a perovskite-type oxide crystal structure which satisfies the following composition formula.

$$La_a M_b Ni_c O_x \quad (1)$$

In the composition formula, the element M represents at least one element selected from Co and Fe, a+b+c=1, and $1.25 \leq x \leq 1.75$. The coefficients a, b, and c preferably satisfy the following relations.

$$0.4595 \leq a \leq 0.535 \quad (2a)$$

$$0.200 \leq b \leq 0.475 \quad (2b)$$

$$0.025 \leq c \leq 0.350 \quad (2c)$$

A perovskite-type electrically conductive oxide having a composition represented by the above-described composition formula has an electrical conductivity of 250 S/cm or greater at room temperature (25° C.) and has a B constant of 600 K or less. Therefore, such a perovskite-type electrically conductive oxide has good characteristics; i.e., has a higher electrical conductivity and a smaller B constant as compared with the case where the above-described relations are not satisfied. Also, since the perovskite-type electrically conductive oxide has a lower activation energy of the interface resistance as compared with a noble metal electrode, the interface resistance can be reduced sufficiently even at low temperatures. Notably, when a Pt electrode is subjected to an air atmosphere at a temperature of about 600° C., the Pt electrode is oxidized and the interface resistance increases. In contrast, the perovskite-type electrically conductive oxide has an advantage that such a time-course change is less likely to occur.

The coefficients b and c more preferably satisfy the following relations (3b) and (3c) instead of the above-described relations (2b) and (2c).

$$0.200 \leq b \leq 0.375 \quad (3b)$$

$$0.125 \leq c \leq 0.300 \quad (3c)$$

In this case, the perovskite-type electrically conductive oxide can have a higher electrical conductivity and a smaller B constant.

The coefficient x of O (oxygen) in the above-described formula (1) is theoretically 1.5 in the case where all the electrically conductive oxide having the above-described composition is formed of the perovskite phase. However, since the proportion of oxygen may deviate from the stoichiometric composition, as a typical example, the range of x is defined to be $1.25 \leq x \leq 1.75$.

Notably, the electrically conductive oxide layer OCL2 may further contain an oxide in addition to the perovskite phase having the above-described composition. For example, the electrically conductive oxide layer OCL2 may contain the perovskite phase and ceria to which a rare earth element oxide other than ceria is added (hereinafter referred to as "rare earth element-added ceria"). Notably, in the following description, the rare earth element-added ceria will be also referred to as a "co-material." For example, $La_2O_3$, $Gd_2O_3$, $Sm_2O_3$, and/or $Y_2O_3$ may be used as a rare earth element oxide other than ceria. The proportion of the rare earth element RE in the rare earth element-added ceria may be determined such that the molar fraction of the rare earth element RE; i.e., the value of $\{RE/(Ce+RE)\}$, falls within the range of, for example, 10 mol % to 50 mol %. Also, the volume ratio of the rare earth element-added ceria in the electrically conductive oxide layer OCL2 may be set to fall within the range of, for example, 10 vol % to 40 vol %. Although such a rare earth element-added ceria is an insulator at low temperatures (room temperature), it functions as a solid electrolyte having oxygen-ion conductivity at high temperatures (temperatures at which the gas sensor 300 is used). Accordingly, when the electrically conductive oxide layer OCL2 contains the rare earth element-added ceria, it is possible to lower the interface resistance of the electrically conductive oxide layer OCL2 while using the gas sensor 300. However, in order to lower the electrical resistance at room temperature, desirably, the electrically conductive oxide layer OCL2 contains no rare earth element-added ceria.

The electrically conductive oxide layer OCL2 may contain an alkaline earth metal element in a very small amount so long as the alkaline earth metal element does not affect the electrical conductivity of the electrically conductive oxide layer OCL2. However, preferably, the electrically conductive oxide layer OCL2 is substantially free of alkaline earth metal element. In such a case, even when the electrically conductive oxide layer OCL2 is exposed to a wide range of temperature ranging from room temperature to a temperature near 900° C. while using the gas sensor 300, a change in the weight of the electrically conductive oxide layer OCL2; i.e., absorption or release of oxygen, becomes less likely to occur. As a result, the electrically conductive oxide layer OCL2 which is suitable for use in a high temperature environment is obtained. Notably, in the present specification, "substantially free of alkaline earth metal element" means that no alkaline earth metal element can be detected or identified by x-ray fluorescence analysis (XRF).

FIG. 2D is an explanatory view showing, on an enlarged scale, the sectional structure of the inside lead portion 210. The inside lead portion 210 has a multilayer structure which includes a lanthanum zirconate layer LZL formed on the inner surface of the solid electrolyte member 11 and an electrically conductive oxide layer OCL1 formed on the inner surface side of the lanthanum zirconate layer LZL. The electrically conductive oxide layer OCL1 may have a composition approximately the same as that of the electrically conductive oxide layer OCL2 of the above-described inside detection electrode portion 220. However, the proportion of the rare earth element-added ceria in the electrically conductive oxide layer OCL2 which constitutes the inside detection electrode portion 220 is desirably equal to or greater than that of the rare earth element-added ceria in the electrically conductive oxide layer OCL1 which constitutes the inside lead portion 210. This is because when the proportion of the rare earth element-added ceria in the inside detection electrode portion 220 is increased, the inside detection electrode portion 220 has a porous structure which increases the area of the tri-phase interface and lowers the interface resistance. Also, in the inside lead portion 210, when the proportion of the rare earth element-added ceria is decreased, the inside lead portion 210 has a dense structure. This enhances electron conductivity and increases the strength of the inside lead portion 210, whereby its impact resistance is further enhanced.

The lanthanum zirconate layer LZL is formed while firing of the inside lead portion 210 as a result of reaction between lanthanum (La) contained in the electrically conductive oxide layer OCL1 and $ZrO_2$ contained in the solid electrolyte member 11. Such a lanthanum zirconate layer LZL will also be referred to as a "reaction layer LZL." Formation of the lanthanum zirconate layer LZL enhances the adhesion between the lanthanum zirconate layer LZL and the electrically conductive oxide layer OCL1 and also the adhesion between the lanthanum zirconate layer LZL and the solid electrolyte member 11, whereby the impact resistance is enhanced. Therefore, in a region where the inside lead portion 210 is present, the lanthanum zirconate layer LZL is preferably formed between the electrically conductive oxide layer OCL1 and the solid electrolyte member 11 in order to enhance the impact resistance.

Notably, since the lanthanum zirconate layer LZL does not have oxygen-ion conductivity, the lanthanum zirconate layer LZL preferably is not formed in the inside detection electrode portion 220 (FIG. 2C). However, a thin lanthanum zirconate layer LZL may be formed in the inside detection electrode portion 220 so long as the secured oxygen-ion conductivity is practically sufficient. In other words, the inside detection electrode portion 220 is preferably formed in such a manner that (i) the lanthanum zirconate layer LZL is not formed between the electrically conductive oxide layer OCL2 and the solid electrolyte member 11, or (ii) the lanthanum zirconate layer LZL formed between the electrically conductive oxide layer OCL2 and the solid electrolyte member 11 is thinner than the lanthanum zirconate layer LZL formed between the solid electrolyte member 11 and the electrically conductive oxide layer OCL1 of the inside lead portion 210. In this case, since the lanthanum zirconate layer which is a high resistance layer is formed, the interface resistance between the electrically conductive oxide layer OCL2 and the solid electrolyte member 11 is restrained from increasing excessively.

FIGS. 3A to 3D are explanatory views showing a gas sensor element 10a according to another embodiment. The gas sensor element 10a shown in FIGS. 3A to 3D differs from the gas sensor element 10 shown in FIGS. 2A to 2D only in two points; i.e., the sectional structure at the position of the inside detection electrode portion 220a (FIG. 3C) and the position of the interface between the inside detection electrode portion 220a and the inside lead portion 210 (FIG. 3B). As to other structural features, the gas sensor element 10a shown in FIGS. 3A to 3D is the same as the gas sensor element 10 shown in FIGS. 2A to 2D. As shown in FIG. 3C, the inside detection electrode portion 220a has a multilayer structure which includes a reaction prevention layer BL formed on the inner surface of the solid electrolyte member 11 and the electrically conductive oxide layer OCL2. The reaction prevention layer BL is an oxide layer formed of the rare earth element-added ceria. As described above, the rare earth element-added ceria functions as a solid electrolyte having oxygen-ion conductivity at high temperatures. In view of the characteristics of the reaction prevention layer BL, the inside detection electrode portion 220a may be considered to have a single-layer structure of the electrically conductive oxide layer OCL2, and the reaction prevention layer BL is formed between the inside detection electrode portion 220a (=OCL2) and the solid electrolyte member 11. The function of the reaction prevention layer BL is to deter the reaction between La in the electrically conductive oxide layer OCL2 and $ZrO_2$ in the solid electrolyte member 11. By providing the reaction prevention layer BL, formation of the lanthanum zirconate layer LZL is advantageously restrained even in the case where firing is performed under conditions under which the lanthanum zirconate layer LZL (reaction layer) may be formed if the reaction prevention layer BL does not exist.

FIGS. 4A to 4D are explanatory views showing a gas sensor element 10b according to yet another embodiment. The gas sensor element 10b shown in FIGS. 4A to 4D differs from the gas sensor element 10a shown in FIGS. 3A to 3D only in two points; i.e., the sectional structure at the position of the inside detection electrode portion 220b (FIG. 4C) and the compositions of the electrically conductive oxide layers OCL1b and OCL2b. As for other structural features, the gas sensor element 10b shown in FIGS. 4A to 4D is the same as the gas sensor element 10a shown in FIGS. 3A to 3D. As shown in FIG. 4C, the inside detection electrode portion 220b has a multilayer structure which includes a reaction prevention layer BL formed on the inner surface of the solid electrolyte member 11, an intermediate electrically conductive layer ICL formed on the inner surface of the reaction prevention layer BL, and the electrically conductive oxide layer OCL2b. Notably, in the case where the reaction prevention layer BL is considered to be different from the inside detection electrode portion 220b described in the embodiment of FIGS. 3A to 3D, the inside detection electrode portion 220b has a double-layer structure composed of the intermediate electrically conductive layer ICL and the electrically conductive oxide layer OCL2b. This structure is obtained by adding the intermediate electrically conductive layer ICL to the structure shown in FIG. 3C. The intermediate electrically conductive layer ICL preferably contains the perovskite phase as a main component, and contains the rare earth element-added ceria as a secondary component. Like the electrically conductive oxide layers OCL1 and OCL2 used in the gas sensor elements shown in FIGS. 2A to 2D and 3A to 3D, the intermediate electrically conductive layer ICL has both ion conductivity and electron conductivity at high temperatures (during use of the gas sensor 300). Therefore, the intermediate electrically conductive layer ICL exhibits a sufficiently low interface resistance. Also, in this structure, the electrically conductive oxide layers OCL1b and OCL2b may be formed by the perovskite phase, but only without adding the rare earth element-added ceria. In such a case, since the electron conductivities of the electrically conductive oxide layers OCL1b and OCL2b at room temperature increase, the electrical resistance can be lowered.

B. Manufacturing Method

Figure 5:
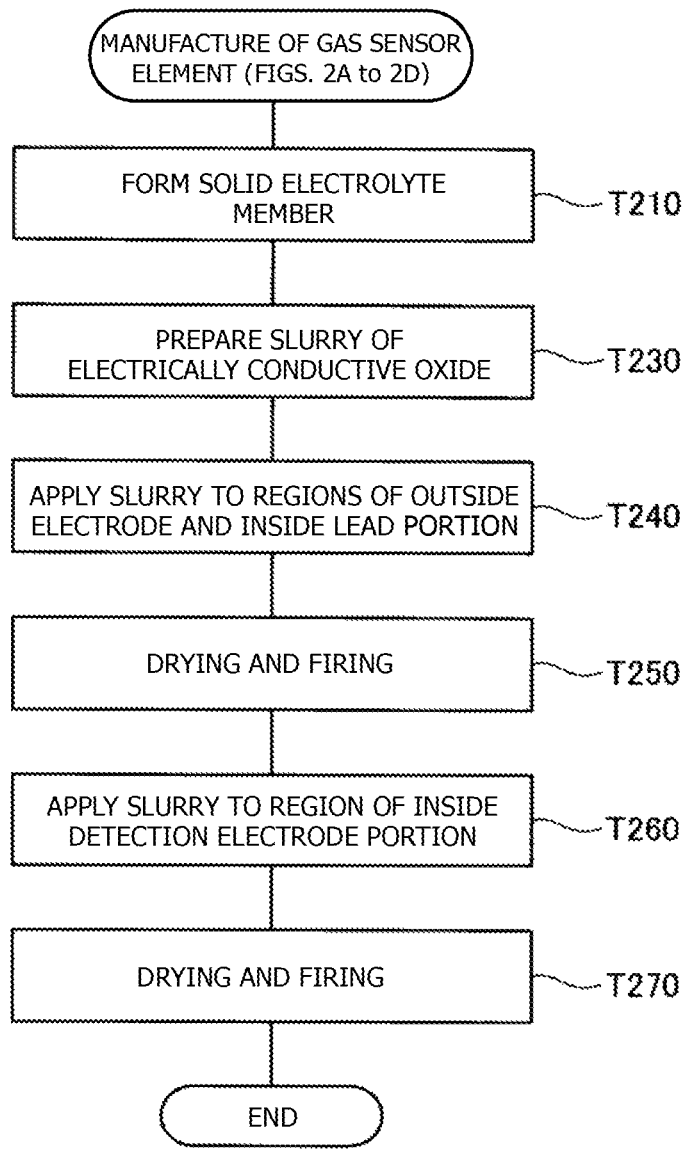
FIG. 5 is a flowchart showing a method of manufacturing the gas sensor element shown in FIG. 2.

FIG. 5 is a flowchart showing a method of manufacturing the gas sensor element 10 shown in FIGS. 2A to 2D. In step T210, the material (e.g., powder of yttria-stabilized zirconia) of the solid electrolyte member 11 is pressed to obtain a compact, which is then machined into a shape (tubular shape) shown in FIG. 2A, whereby a green body (green compact) is obtained. In step T230, a slurry of electrically conductive oxide is prepared. In step T230, for example, raw material powders of the electrically conductive oxides are weighed and wet-mixed, and the resultant mixture is dried, whereby a raw material powder mixture is prepared. For example, $La(OH)_3$ or $La_2O_3$; and $Co_3O_4$, $Fe_2O_3$, and NiO may be used as the raw material powder of the perovskite phase. Also, $CeO_2$ and $La_2O_3$, $Gd_2O_3$, $Sm_2O_3$, $Y_2O_3$, etc., may be used as the raw material powder of the rare earth element-added ceria. The mixture of these raw material powder is pre-fired at 700 to 1,200° C. for 1 to 5 hours in the atmosphere, whereby a pre-fired powder is prepared. This pre-fired powder is pulverized to a predetermined grain size using, for example, a wet ball mill, and is dissolved, together with a binder such as ethyl cellulose, in a solvent such as terpineol or butyl carbitol, whereby a slurry is prepared.

In step T240, a slurry of a noble metal oxide such as a Pt paste is applied to a region in which the outside electrode 100 (FIG. 2A) is to be formed, and the slurry of an electrically conductive oxide is applied to a region where the inside lead portion 210 (FIG. 2B) to be formed. At that time, in order to prevent the slurry of electrically conductive oxide from being applied to a region where the inside detection electrode portion 220 is to be formed, a masking member is preferably applied to that region in advance. In step T250, after drying, the green compact is fired at a firing temperature of, for example, 1,250° C. to 1,450° C. (preferably, 1,350±50° C.). At that time, as shown in FIG. 2D, the lanthanum zirconate layer LZL is formed between the electrically conductive oxide layer OCL1 of the inside lead portion 210 and the solid electrolyte member 11. As described above, the lanthanum zirconate layer LZL is a layer formed as a result of a reaction between lanthanum (La) contained in the electrically conductive oxide layer OCL1 and $ZrO_2$ contained in the solid electrolyte member 11. Notably, the higher the firing temperature and the smaller the proportion of the rare earth element-added ceria, the greater the thickness of the lanthanum zirconate layer LZL. Accordingly, the thickness of the lanthanum zirconate layer LZL can be adjusted by adjusting these parameters.

In step T260, the slurry of electrically conductive oxide is applied to a region where the inside detection electrode portion 220 (FIG. 2B) is to be formed. In step T270, after drying, firing is performed at a firing temperature of, for example, 800° C. to 1,050° C. (preferably, 1,000±50° C.). When the firing temperature in step T260 is limited to 1,050° C. or lower, the lanthanum zirconate layer LZL is not formed at all or is formed to have a thickness smaller than that of the lanthanum zirconate layer formed in the inside lead portion 210. As a result, as shown in FIG. 2C, the lanthanum zirconate layer LZL is hardly formed between the electrically conductive oxide layer OCL2 of the inside detection electrode portion 220 and the solid electrolyte member 11.

Figure 6:
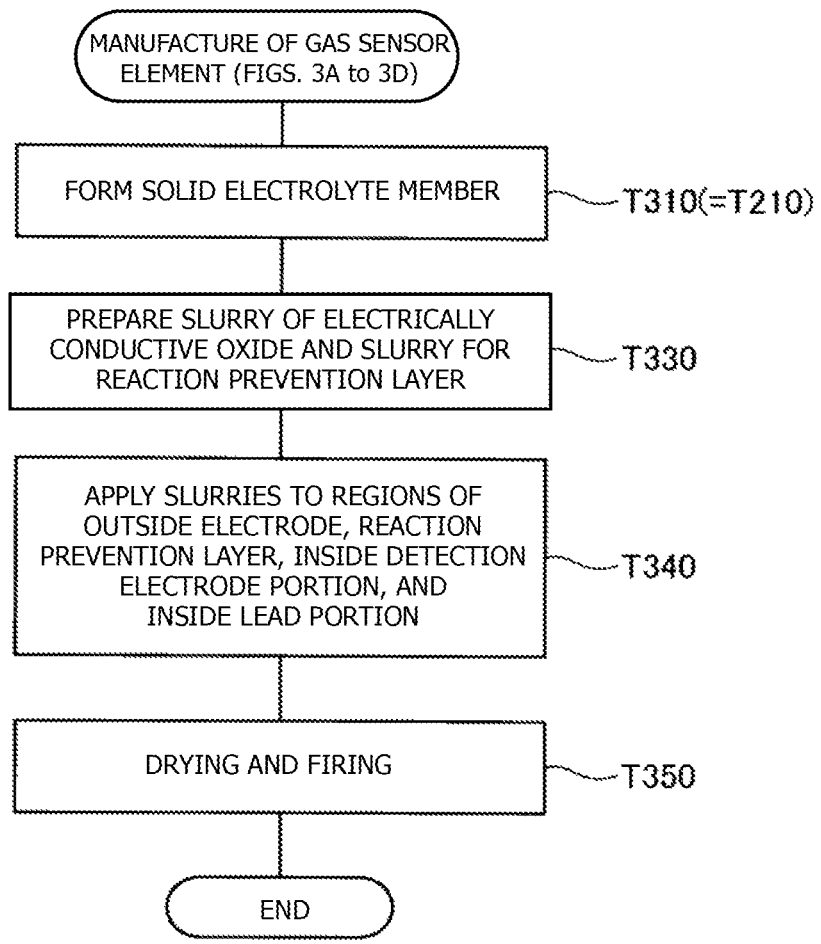
FIG. 6 is a flowchart showing a method of manufacturing the gas sensor element shown in FIG. 3.

FIG. 6 is a flowchart showing a method of manufacturing the gas sensor element 10a shown in FIGS. 3A to 3D. Step T310 is the same as step T210 of FIG. 5. In step T330, the slurry of electrically conductive oxide and the slurry for the reaction prevention layer BL (FIG. 3C) are Obtained. The slurry of electrically conductive oxide is the same as that prepared in step T230 of FIG. 5. As described above, a reaction prevention layer BL is formed of the rare earth element-added ceria. Accordingly, the slurry for the reaction prevention layer BL is prepared by dissolving a commercially available rare earth element ($La_2O_3$, $Gd_2O_3$, $Sm_2O_3$, $Y_2O_3$, etc.) added ceria, together with a binder such as ethyl cellulose, in a solvent such as terpineol or butyl carbitol. The rare earth element-added ceria is prepared by a solid phase method or a co-precipitation method. In step T340, the slurry of a noble metal oxide such as a Pt paste is applied to a region in which the outside electrode 100 (FIG. 3A) is to be formed, and slurry of rare earth element-added ceria is applied to a region where the reaction prevention layer BL is to be formed. Also, the slurry of electrically conductive oxide is applied to cover a region where the inside lead portion 210 (FIG. 3B) is to be formed and a region on the inner surface side of the reaction prevention layer BL where the inside detection electrode portion 220a (FIG. 3C) is to be formed. In this case, the inside detection electrode portion 220a and the inside lead portion 210 are formed of the same electrically conductive oxide. Notably, in the case where the composition of the electrically conductive oxide of the inside detection electrode portion 220a is made different from that of the electrically conductive oxide of the inside lead portion 210, slurries having different compositions are applied to the respective regions.

In step T350, after drying, the green compact is fired at a firing temperature of, for example, 1,250° C. to 1,450° C. (preferably, 1,350±50° C.). At that time, since the reaction prevention layer BL is present between the electrically conductive oxide layer OCL1 of the inside detection electrode portion 220a and the solid electrolyte member 11 as shown in FIG. 3C, the lanthanum zirconate layer LZL is not formed. Since the steps of FIG. 6 include a fewer number of firing steps as compared with the steps of FIG. 5, the manufacturing method shown in FIG. 6 has an advantage of shortening the overall production time.

Figure 7:
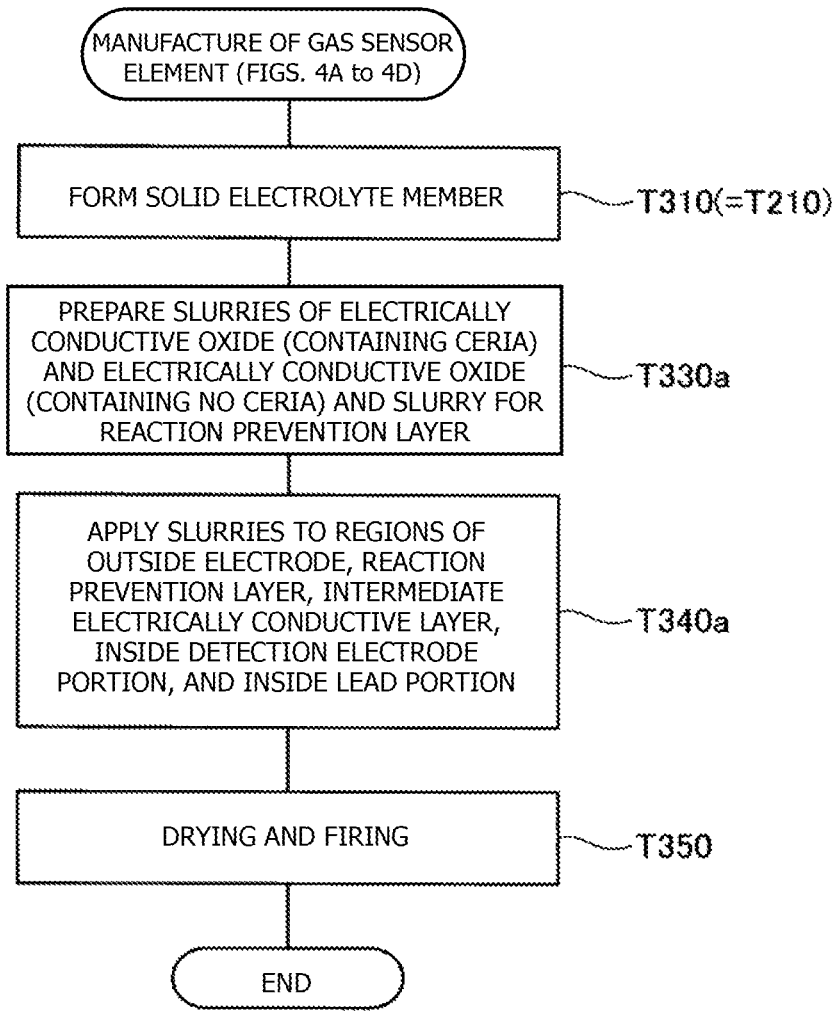
FIG. 7 is a flowchart showing a method of manufacturing the gas sensor element shown in FIG. 4.
Figure 8A:
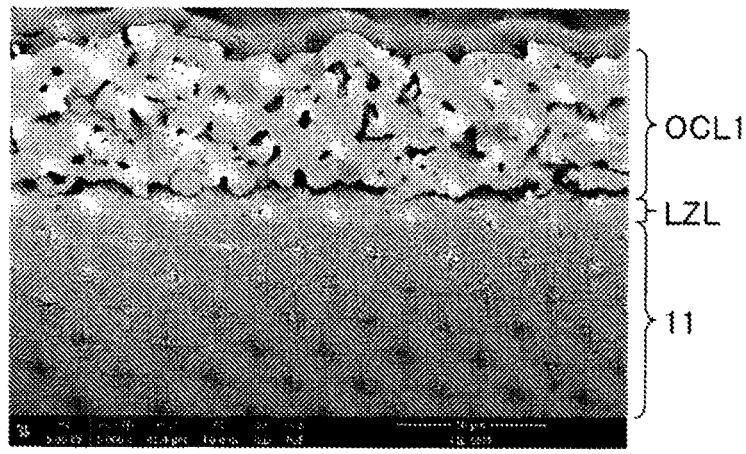
FIGS. 8A to 8D are cross-sectional SEM images of samples tested in the mechanical impact resistance test.
Figure 8B:
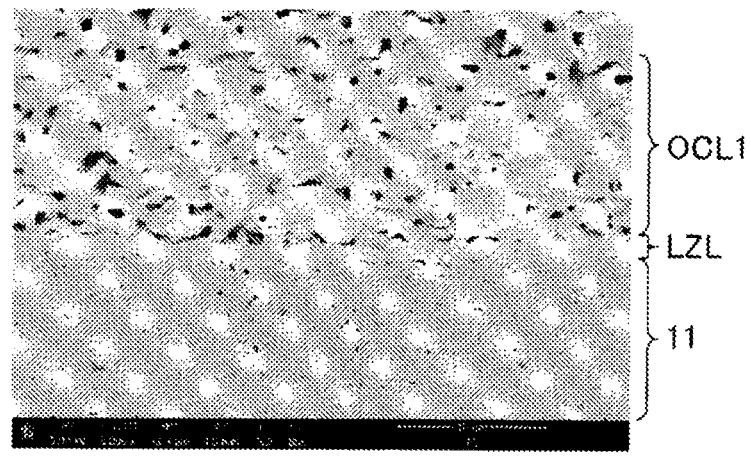
Figure 8C:
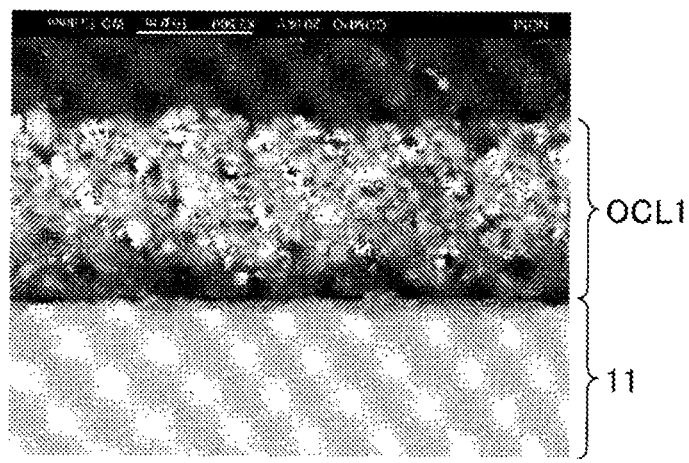
Figure 8D:
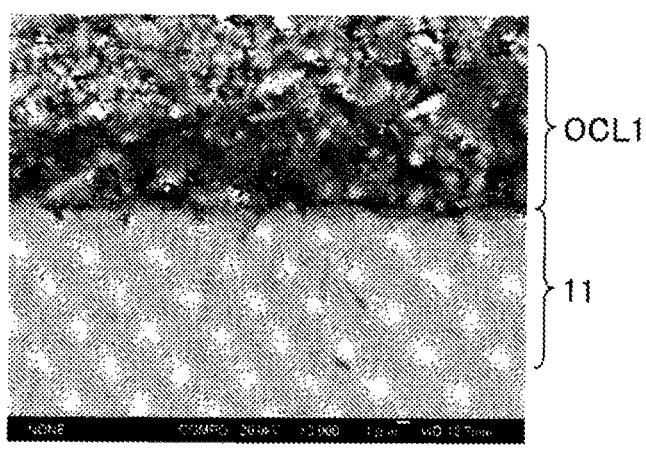

FIG. 7 is a flowchart showing a method of manufacturing the gas sensor element 10b shown in FIGS. 4A to 4D. The manufacturing method shown in FIG. 7 is the same as the manufacturing method shown in FIG. 6 except for two steps; i.e., steps T330a and T340a. Step T330a of FIG. 7 differs from step T330 of FIG. 6 in that, in step T330a, two types of slurries of electrically conductive oxides; i.e., a slurry of electrically conductive oxide which contains a rare earth element-added ceria and a slurry of electrically conductive oxide which contains no rare earth element-added ceria, are prepared. Step T340a of FIG. 7 differs from step T340 of FIG. 6 in that, in step T340a, after applying the slurry for the reaction prevention layer BL, the slurry for the intermediate electrically conductive layer ICL (FIG. 4C) is applied, and then the slurry for the electrically conductive oxide layer OCL2b of the inside detection electrode portion 220b is applied. As described above, the intermediate electrically conductive layer ICL contains the perovskite phase and the rare earth element-added ceria. Meanwhile, the electrically conductive oxide layer OCL2b contains no rare earth element-added ceria and is formed of the perovskite phase only. Therefore, in step T340a, the two types of slurries of electrically conductive oxides and the slurry for the reaction prevention layer BL prepared in step T330a are used so as to apply a slurry that is suitable for each region. Thus, it becomes possible to obtain the structure shown in FIGS. 4A to 4D by firing the green compact at a firing temperature of, for example, 1,250° C. to 1,450° C. (preferably, 1,350±50° C.) in step T350.

Notably, the various manufacturing conditions employed in the manufacturing methods shown in FIGS. 5 to 7 are mere examples, and can be freely changed in accordance with an intended use of products and the like.

C. Mechanical Impact Resistance Test

Table 1 below shows the results of a test regarding the mechanical impact resistance (impact resistance) of the inside lead portion 210. Samples S01 and S02 are examples, and samples S03 and S04 whose sample numbers are denoted by an asterisk are comparative examples. Yttria-added zirconia (5YSZ) (yttria: 5 mol %) was used for the solid electrolyte member 11 of each sample. When each sample was made, a slurry for the electrically conductive oxide layer OCL1 was applied to a portion of the solid electrolyte member 11 corresponding to the inside lead portion 210 and dried. This slurry was prepared by mixing a powder of the perovskite-type electrically conductive oxide having a composition represented by the above-described formula (1), gadolinium-added ceria (GDC) serving as a secondary component, a binder, and an organic solvent. As shown in Table 1, $LaCo_{0.5}Ni_{0.5}O_3$ (referred to as "LCN") or $LaFe_{0.5}Ni_{0.5}O_3$ (referred to as "LFN") was used as a powder of electrically conductive oxide. The gadolinium content of the gadolinium-added ceria was 20 mol %. The proportion of the gadolinium-added ceria in the electrically conductive oxide layer OCL1 was set to 30 vol %. For preparation of samples S01 and S02, the slurry was applied to the green compact of the solid electrolyte member 11 and dried, and the green compact was fired at 1,350° C. for one hour. Meanwhile, for preparation of samples S03 and S04, the green compact of the solid electrolyte member 11 was fired at 1,350° C. for one hour, the slurry was applied and dried, and then firing was performed at 1,000° C. for one hour.

TABLE 1

TESTING OF MECHANICAL IMPACT RESISTANCE
OF INSIDE LEAD PORTION

| Sample No. | Composition and firing temperature of inside lead portion 210 | | | | Damage to lead portion |
|---|---|---|---|---|---|
| | Perovskite phase | Co-matrix | Reaction layer LZL | Firing temperature | |
| S01 | LCN | GDC (30 vol %) | Provided | 1350° C. | Not observed |
| S02 | LFN | GDC (30 vol %) | Provided | 1350° C. | Not observed |
| S03* | LCN | GDC (30 vol %) | Not provided | 1000° C. | Observed |
| S04* | LFN | GDC (30 vol %) | Not provided | 10000° C. | Observed |

LCN = $LaCo_{0.5}Ni_{0.5}O_3$
LFN = $LaFe_{0.5}Ni_{0.5}O_3$
GDC = 20 mol % Gd—$CeO_2$ FIGS. 8A to 8D show cross-sectional SEM images of the interface between the electrically conductive oxide layer OCL1 of the inside lead portion 210 and the solid electrolyte member 11 for samples S01 to S04. The SEM images show that whereas the reaction layer LZL (the lanthanum zirconate layer) is present in samples S01 and S02 (examples), the reaction layer LZL is not present in samples S03 and S04 (comparative examples). This difference occurs because the firing temperature was set to 1,350° C. for samples S01 and S02 and set to 1,000° C. for samples S03 and S04. Namely, by setting the firing temperature to a temperature higher than 1,000° C., the reaction layer LZL (the lanthanum zirconate layer) can be formed between the electrically conductive oxide layer OCL1 and the solid electrolyte member 11. Notably, for forming the reaction layer LZL, the firing temperature is preferably set to a temperature of 1,250° C. to 1,450° C., more preferably, to 1350±50° C.

In the mechanical impact resistance test, the connection terminal 70 formed of SUS (FIG. 1) was used, and the insertion and removal of the connection terminal 70 was repeated 30 times. Afterwards, each sample was cut into halves, and a portion of the inside lead portion 210 with which the connection terminal 70 came into contact was observed with a magnifying glass. In samples S01 and S02 (examples), damage to the inside lead portion 210 was not observed. In samples S03 and S04 (comparative examples), separation of the inside lead portion 210 occurred (see the right end of Table 1). Presumably, the reason why damage to the inside lead portion 210 was not observed in samples S01 and S02 (examples) is that in samples S01 and S02, the reaction layer LZL functions as an adhesive layer between the electrically conductive oxide layer OCL1 and the solid electrolyte member 11 as described with reference to FIG. 2D. Consequently, the interface becomes strong. As understood from the test results, from the viewpoint of enhancing the impact resistance of the inside electrode 200, the reaction layer LZL (the lanthanum zirconate layer) is preferably formed between the electrically conductive oxide layer OCL1 of the inside lead portion 210 and the solid electrolyte member 11.

D. Electrode Interface Resistance Measurement

Table 2 below shows the results of a test in which the electrode interface resistance was measured for gas sensor elements having the structures shown in FIGS. 2A to 2D and 3A to 3D. Samples S11 to S15 are examples, and sample S16 whose sample number is denoted by an asterisk is a comparative example. Table 2 shows the composition and firing temperature of the inside detection electrode portion 220, the composition and firing temperature of the inside lead portion 210, and the measured electrode interface resistance for each sample. In the composition columns, compositions are shown in a simplified manner. For example, the composition of the inside detection electrode portion 220 (i.e., the electrically conductive oxide layer OCL2) of sample Sit is such that 30 vol % GDC (gadolinium-added ceria containing 20 mol % gadolinium) which is a secondary component is added to LCN ($LaCo_{0.5}Ni_{0.5}O_3$) which is a main component. Notably, in samples S14 and S15, the reaction prevention layer BL (FIG. 3(C)) is provided in the inside detection electrode portion 220. However, in other samples S11 to S13 and S16, the reaction prevention layer BL is not provided. Yttria-stabilized zirconia (5YSZ) including 5 mol % yttria was used for the solid electrolyte member 11 of each sample.

Samples S11 to S13 were made in accordance with the procedure shown in FIG. 5. In step T240 of FIG. 5, slurry prepared by mixing 30 vol % of yttria-stabilized zirconia (5YSZ) into powder of platinum (Pt) was used as a slurry for the outside electrode 100. Also, slurries having the compositions shown in FIG. 10 were selectively used as a slurry for the inside lead portion 210. In step T250 of FIG. 5, firing was performed at 1,350° C., and in step T270, firing was performed at 1,000° C. As a result, the gas sensor elements of samples S11 to S13 each having the structure shown in FIGS. 2A to 2D were obtained.

Samples S14 and S15 were made in accordance with the procedure shown in FIG. 6. A slurry prepared by mixing 30 vol % of yttria-stabilized zirconia (5YSZ) into powder of platinum (Pt) was used as a slurry for the outside electrode 100. Also, slurries having the compositions shown in Table 2 were used as slurries for other portions. In step T350 of the reaction layer LZL was formed in the inside detection electrode portion 220. Also, in all samples S11 to S16, the reaction layer LZL was formed in the inside lead portion 210.

By using the other of the two elements made for each of samples S11 to S16, the electrode interface resistance was measured. Namely, the element of each sample was disposed in a furnace such that the temperature of the element became 550° C., and the electrode interface resistance was measured by an AC impedance method. The amplitude of voltage for the measurement was set to 10 mV.

TABLE 2

MEASUREMENT OF ELECTRODE INTERFACE RESISTANCE

| Sample No. | Composition and firing temperature of inside detection electrode portion 220 | | | | Composition and firing temperature of inside lead portion 210 | | | Electrode interface resistance [Ω] |
|---|---|---|---|---|---|---|---|---|
| | Composition | Reaction prevention layer BL | Reaction layer LZL | Firing temperature | Composition | Reaction layer LZL | Firing temperature | |
| S11 | LCN/GDC (30 vol %) | Not provided (FIG. 2C) | Not Provided | 1000° C. | LCN/GDC (30 vol %) | Provided | 1350° C. | 55 |
| S12 | LCN/GDC (30 vol %) | Not provided (FIG. 2C) | Not provided | 1000° C. | LCN/GDC (30 vol %) | Provided | 1350° C. | 52 |
| S13 | LFN/GDC (30 vol %) | Not provided (FIG. 2C) | Not provided | 1000° C. | LFN/GDC (30 vol %) | Provided | 1350° C. | 172 |
| S14 | LCN/GDC (30 vol %) | GDC (FIG. 3C) | Not provided | 1350° C. | LCN/GDC (30 vol %) | Provided | 1350° C. | 135 |
| S15 | LFN/GDC (30 vol %) | GDC (FIG. 3C) | Not provided | 1350° C. | LFN/GDC (30 vol %) | Provided | 1350° C. | 420 |
| S16* | LCN/GDC (30 vol %) | Not provided | Provided | 1350° C. | LCN/GDC (30 vol %) | Provided | 1350° C. | 2505 |

LCN = $LaCo_{0.5}Ni_{0.5}O_3$
LFN = $LaFe_{0.5}Ni_{0.5}O_3$
GDC = 20 mol % Gd—$CeO_2$
LDC = 40 mol % La—$CeO_2$ FIG. 6, firing was performed at 1,350° C. As a result, the gas sensor elements of samples S14 and S15 each having the structure shown in FIGS. 3A to 3D were obtained.

Sample S16 (comparative example) was also made in accordance with the procedure shown in FIG. 6. A slurry prepared by mixing 30 vol % of yttria-stabilized zirconia (5YSZ) into a powder of platinum (Pt) was used as a slurry for the outside electrode 100. Also, slurries having the compositions shown in FIG. 10 were used as slurries for other portions. However, in sample S16, the slurry for the reaction prevention layer BL was not applied. In step T350 of FIG. 6, firing was performed at 1,350° C. As a result, an element in which the reaction layer LZL (the lanthanum zirconate layer) was formed in both the inside detection electrode portion 220 and the inside lead portion 210 was obtained as the gas sensor element of sample S16.

Figure 9:
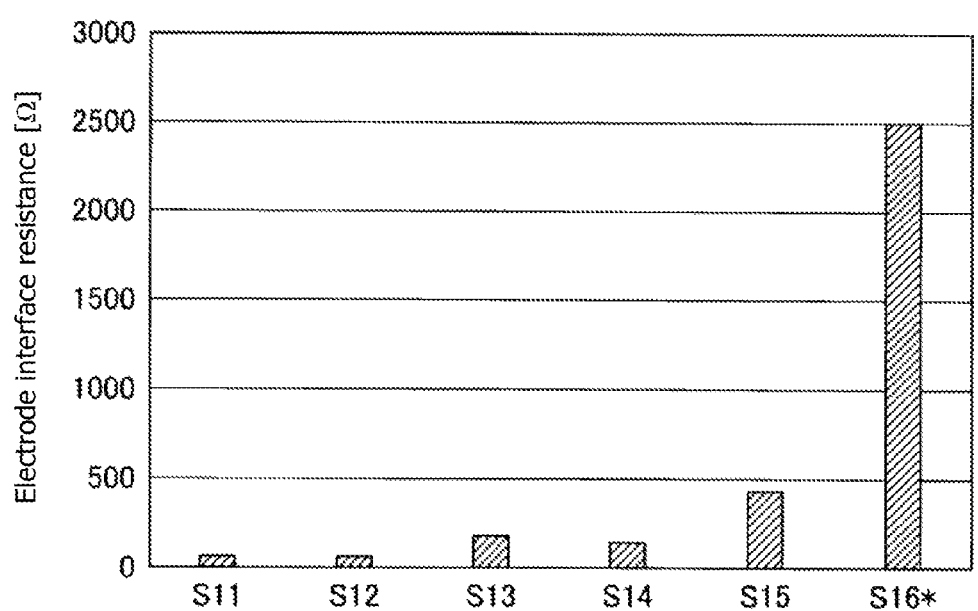
FIG. 9 is a graph showing the results of electrode interface resistance measurement.

For each of the above-described samples S11 to S16, two elements were made. The cross section of one of the two obtained elements was observed under an SEM (scanning electron microscope). Further, the state of the reaction layer LZL between the inside detection electrode portion 220 and the solid electrolyte member 11 and the state of the reaction layer LZL between the inside lead portion 210 and the solid electrolyte member 11 were checked. Namely, the presence/absence of the reaction layer LZL and the thickness of the reaction layer LZL were investigated by observing SEM backscattered electron images and by EDS (energy dispersive X-ray spectrometry). As shown in Table 2, in samples S11 to S15, the reaction layer LZL was not formed in the inside detection electrode portion 220, and in sample S16, FIG. 9 is a graph showing the results of measuring the electrode interface resistances of samples S11 to S16. Whereas the electrode interface resistances of samples S11 to S15 are 500Ω or less and are sufficiently small from a practical viewpoint, the electrode interface resistance of sample S16 (comparative example) is greater than 2,000Ω and is very high. As understood from these results, the electrode interface resistance can be reduced sufficiently and the internal resistance of the gas sensor element can be lowered by employing the structure of FIGS. 2A to 2D or FIGS. 3A to 3D in which the reaction layer LZL (the lanthanum zirconate layer) is not formed in the inside detection electrode portion 220.

Modifications:
Notably, the present invention is not limited to the above-described examples and embodiments and can be implemented in various forms without departing from the scope of the invention.

Modification 1:
In the above-described embodiments, an oxygen concentration sensor has been described as an example of the gas sensor of the present invention. However, the present invention can be applied to an oxygen sensor including a plate-shaped gas sensor element and a gas sensor for a gas other than oxygen.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-139520 filed Jul. 13, 2015, the above-noted application incorporated herein by reference in its entirety.

What is claimed is:

1. A gas sensor element comprising:
a solid electrolyte member extending in an axial direction and containing $ZrO_2$ having oxygen-ion conductivity;
an outside electrode provided on one of surfaces of the solid electrolyte member and which comes into contact with a gas under measurement; and
an inside electrode provided on an opposing surface of the solid electrolyte member and which comes into contact with a reference gas,
the inside electrode including an inside detection electrode portion disposed on a forward end side in the axial direction and which detects a particular gas contained in the gas under measurement, and an inside lead portion which is disposed rearward of the inside detection electrode portion, which is connected to the inside detection electrode portion, and which comes into contact with a connection terminal for external output, wherein
the inside electrode includes an electrically conductive oxide layer whose main component is a perovskite phase which is represented by a composition formula of $La_aM_bNi_cO_x$ (where M is at least one element selected from Co and Fe, a+b+c=1, $1.25 \leq x \leq 1.75$) and has a perovskite-type crystal structure;
the coefficients a, b, and c satisfy $0.459 \leq a \leq 0.535$, $0.200 \leq b \leq 0.475$, and $0.025 \leq c \leq 0.350$;
the inside lead portion includes a lanthanum zirconate layer between the electrically conductive oxide layer and the solid electrolyte member; and
the inside detection electrode portion is formed such that (i) no lanthanum zirconate layer is formed between the electrically conductive oxide layer and the solid electrolyte member, or (ii) a lanthanum zirconate layer formed between the electrically conductive oxide layer and the solid electrolyte member is thinner than the lanthanum zirconate layer of the inside lead portion.

2. The gas sensor element as claimed in claim 1, wherein a reaction prevention layer containing a rare earth element-added ceria as a main component is provided between the inside detection electrode portion and the solid electrolyte member.

3. The gas sensor element as claimed in claim 2, wherein the reaction prevention layer is provided only on the forward end side of the gas sensor element with respect to a holding member which holds the gas sensor element when the gas sensor element is incorporated into a gas sensor.

4. The gas sensor element as claimed in claim 1, wherein
the inside detection electrode portion has an intermediate electrically conductive layer formed between the reaction prevention layer and the electrically conductive oxide layer,
the electrically conductive oxide layer contains no rare earth element-added ceria and comprises a perovskite phase represented by the composition formula $La_aM_b$-$Ni_cO_x$, and
the intermediate electrically conductive layer comprises a perovskite phase represented by the composition formula $La_aM_bNi_cO_x$ and a rare earth element-added ceria.

5. The gas sensor element as claimed in claim 1, wherein
the electrically conductive oxide layer contains a first electrically conductive oxide layer which constitutes the inside lead portion and a second electrically conductive oxide layer which constitutes the inside detection electrode portion,
each of the first electrically conductive oxide layer and the second electrically conductive oxide layer contains the perovskite phase and a rare earth element-added ceria, and
the proportion of the rare earth element-added ceria in the second electrically conductive oxide layer is equal to or greater than the proportion of the rare earth element-added ceria in the first electrically conductive oxide layer.

6. A gas sensor comprising:
the gas sensor element as claimed in claim 1; and
a holding member for holding the gas sensor element.

* * * * *